United States Patent
Preston et al.

(12)

(10) Patent No.: US 6,569,632 B1
(45) Date of Patent: May 27, 2003

(54) MONOCLONAL ANTIBODY PROBE FOR DETECTION OF ADHESINS ASSOCIATED WITH MATURE ENDOSPORES OF PASTEURIA SPP

(75) Inventors: James F. Preston, Micanopy, FL (US); Donald W. Dickson, Gainesville, FL (US); John D. Rice, Gainesville, FL (US); Jonathan H. Charnecki, Apex, NC (US); Janete A. Brito, Gainesville, FL (US); Liesbeth M. Schmidt, Lake City, FL (US)

(73) Assignee: University of Florida

( * ) Notice: Subject to any disclaimer, the term of this patent is extended or adjusted under 35 U.S.C. 154(b) by 129 days.

(21) Appl. No.: 09/692,628

(22) Filed: Oct. 19, 2000

(51) Int. Cl.[7] ...................... G01N 33/53; G01N 33/567; G01N 33/554; G01N 33/569
(52) U.S. Cl. ...................... 435/7.1; 435/7.2; 435/7.32; 435/7.92
(58) Field of Search ............................. 424/9.34, 130.1, 424/150.1; 435/7.1, 7.2, 7.32, 7.92

(56) References Cited

U.S. PATENT DOCUMENTS

| 5,089,263 A | 2/1992 | Spiegel et al. |
|---|---|---|
| 5,094,954 A | 3/1992 | Previc |
| 5,248,500 A | 9/1993 | Ayanaba |
| 5,549,729 A | 8/1996 | Yamashita |
| 5,593,668 A | 1/1997 | Nishimuta et al. |
| 5,797,976 A | 8/1998 | Yamashita |
| 5,989,543 A | 11/1999 | Davide et al. |
| 6,063,636 A | * 5/2000 | Stevens et al. |

OTHER PUBLICATIONS

Roe et al. (Protein Purification Techniques Second Edition Chapter 3, Oxford University Press, UK) pp 36–37, 2001.*
Charnecki, J., "Pasteuria Penetrans Spore Proteins: Potential Function In Attachment to Meloidogyne SPP," Master Thesis University of Florida, 1997.
Biochemical Events in the Development of Pasteuria Penetrans, Brito, J.A., Preston, J.F. Giblin–Davis, R.M. and Rice, J.D. *Journal of Nematology*, vol. 30, No. 4, Dec. 1998 p. 9.
Methods for Studying Pasteuria SPP. For Biological Control of Nematodes, Hewlett, D. W. Serracin, M., *Florida Nematology*, vol. 88, No. 9, Sep. 1998, pp 1–9.

* cited by examiner

*Primary Examiner*—Mark Navarro
(74) *Attorney, Agent, or Firm*—Akerman Senterfitt; Stanley A. Kim

(57) ABSTRACT

Disclosed are methods for identifying the presence of Pasteuria endospores in soil and soil extract samples and distinguishing between Pasteuria spp and non-Pasteuria spp in the samples. Also disclosed are methods for identifying the presence of Pasteuria endospores after immobilizing a soil extract or an isolated portion of the soil extract on a substrate. Further, methods for quantifying the approximate number of Pasteuria endospores in a soil sample are described.

27 Claims, No Drawings

MONOCLONAL ANTIBODY PROBE FOR DETECTION OF ADHESINS ASSOCIATED WITH MATURE ENDOSPORES OF PASTEURIA SPP

This invention relates to biocontrol of plant-pathogenic nematodes, and in particular to a monoclonal antibody used in the detection of adhesins associated with mature endospores of *Pasteuria penetrans* isolated from *Meloidogyne arenaria* race 1, and Pasteuria isolates from other phytopathogenic nematodes.

BACKGROUND AND PRIOR ART

The world-wide destructive capacity of nematodes on cultured plants and consequent loss of crop productivity are well known (Sasser, J. N., Plant Disease 64(1): 36–41, 1987). Chemical nematicides, which have been the control method of choice, are rapidly becoming anathematized because of their real and potential adverse impacts on the environment. The need for the development of alternative chemical or bio-rational control agents of nematodes has been widely stated.

The genus Pasteuria was first described by Metchnikoff in 1888 as a parasite of Daphnidae, with the type species designated as *Pasteuria ramosa*. Following a lengthy period of relative obscurity and taxonomic confusion, a new species designation, *Pasteuria penetrans*, was assigned to a bacterial parasite of root-knot nematodes of the genus Meloidogyne (Sayre, R. M., and M. P. Starr, Proceedings of the Helminthology Society, Washington, 52:149–165, 1985). In addition to *P. penetrans*, other species of Pasteuria have been designated on the basis of spore morphology and host preference. These include *Pasteuria nishizawae*, a parasite of the cyst-forming nematodes, e.g. *Heterodera glycines; Pasteuria thornei*, a parasite of lesion nematodes, e.g. Pratylenchus spp., and Pasteuria sp, a parasite of sting nematodes, e.g. *Belanolaimus longicaudatus* (Chen, Z. X., and D. W. Dickson, Journal of Nematology, 30:313–340, 1998). The physiological aspects of the life cycle of *P. penetrans*, and its infection of and propagation in root-knot nematodes, is reasonably well understood. The genetic and biochemical aspects are not well understood. The process (es) by which soil-borne endospores become associated with nematodes in the soil involves recognition of the host by carbohydrate-lectin interactions, followed by irreversible attachment. Glycoproteins have been implicated in this process and have been collectively designated as adhesins (Persidis, A., J. G. Lay, T. Manousis, A. H. Bishop, and D. J. Ellar., Journal of Cell Science, 100:616–622, 1991). The nematode may be infected by an attached spore after it has migrated to a feeding site in a root of a host plant and initiated the formation of giant cells characteristic of the root-knot . Proliferation of the bacteria and their development into endospores occurs in the differentiated female nematode, and results in the formation and ultimate release into the soil of as many as 2 million endospores from a single infected nematode.

Furthermore, endospore-forming bacteria assigned to the Pasteuria genus have been recognized as potential agents for the biocontrol of plant-pathogenic nematodes (Sayre, R. M., Plant Disease 4:527–532, 1980; Stirling, O. R., Phytopathology 74:55–60, 1984). Studies at the University of Florida have established an inverse relationship between the levels of endospores of *Pasteuria penetrans* in the soil and the incidence of infection of peanut by *Meloidogyne arenaria* (Chen, Z. C., and D. W. Dickson, Journal of Nematology, 30:313–340, 1998). This work has provided the strongest evidence that the levels of endospores of *P. penetrans* in the soil are responsible for suppressing the nematode infestation of crop plants in the field. It has provided a basis for developing protocols to suppress nematode infestations through increasing the levels of Pasteuria endospores in the soil. Along with several other studies, this work has indicated that levels Pasteuria endospores at certain levels, e.g. greater than 100,000 per g of soil, may be sufficient to provide adequate protection against infection of plants by phytopathogenic nematodes without treatment with chemical nematicides.

Traditionally, the concentration of soil-borne endospores of Pasteuria is determined using a relatively laborious and time-consuming bioassay procedure, wherein cultivated $2^{nd}$ stage Meloidogyne juveniles (J2) are incubated in a soil sample. The J2's are recovered by centrifugation in sucrose, and the numbers of endospores associated with the nematode cuticle serve as the basis for estimating the number of endospores in the soil sample.

In recent studies at the University of Florida (Gainesville), a monoclonal antibody was developed which was able to bind to intact spores of different isolates of *Pasteuria penetrans*. The binding of the antibody to the spores prevented the spores from binding to the J2 stage of the root-knot nematode. The monoclonal antibody detected an epitope (determinant) that was shared by several polypeptides derived from the spore. It appears that the epitope is involved in the recognition of endospores and their attachment to the nematode, processes that are necessary for the suppression of the nematode infection of plants. The details of this monoclonal antibody, its method of preparation, and further details of this work are contained in the thesis presented by John H. Charnecki to the Graduate School at the University of Florida, August 1997, for the Master of Science degree and was also referenced in Abstract Q-171, entitled "Determinants for the attachment of endospores of *Pasteuria penetrans* to phytopathogenic nematodes", J. H. Charnecki, J. D. Rice, D. W. Dickson, and J. F, Preston on p 449 in the book of abstracts for the 1998 Annual Meetings of the American Society for Microbiology in Atlanta, Ga., May 17 to 21.

Previc et al., U.S. Pat. No. 5,094,954, recognizing the potential use of the bacteria group Pasteuria as biorational control agents against phytopathogenic nematodes, detailed a process for producing endospores of Pasteuria by growing the bacteria on explanted nematode tissue.

There is no way known, other than the referenced method using J2 stage Meloidogyne juveniles, to establish to quality and quantity of the endospores of *Pasteuria penetrans* produced upon growing the bacteria.outside of the nematode host.

It would therefore be highly useful to have a probe or method that could be used to monitor the levels of Pasteuria spores in the soil: would make possible a measure of the relationship between the levels of spores and the extent to which application of chemical nematicides are needed for the suppression of root-knot and other phytopathogenic nematodes; and would make possible knowledgeable production of Pasteuria spores in quantities adequate for their application as biocontrol agents and alternatives to chemical nematicides.

BRIEF SUMMARY OF THE INVENTION

The first objective of the present invention is to provide a probe for the specific and sensitive detection of endospores of Pasteuria spp.

The second objective of this invention is to provide a method for the accurate and sensitive determination of the levels of endospores of *Pasteuria penetrans* in soil samples.

The third objective of this invention is to provide a probe for the detection of adhesins associated with the virulence of mature endospores of Pasteuria spp.

A preferred embodiment of the invention is a probe consisting essentially of a monoclonal antibody (MAb) generated against an epitope carried by endospores of *Pasteuria penetrans* and a method for its use as a probe in detecting the levels of soil-borne Pasteuria endospores comprised of the following steps: mixing a quantity of soil suspected of containing Pasteuria with reagents capable of solublizing the epitope recognized by the MAb; incubating said admixture at a temperature between 37 C and 50 C for a time of 0.5 to 2 hours to allow extraction and solubilization of epitopes; centrifuging to remove debris and provide a soluble preparation of epitopes; quantifying the endospore epitopes with the MAb by ELISA.

*Pasteuria penetrans* is a Gram-positive, endospore-forming, obligate parasite of phytopathogenic root-Inot nematodes, Meloidogyne spp. Regulations restricting the use of the cropland chemical nematicide, methyl bromide, in the U.S. and elsewhere, has prompted renewed search for alternative methods to control these nematode pests. *P. penetrans*, as well as other Pasteuria spp., have so far been unamenable to axenic culture and therefore cannot be isolated and quantified by traditional bacteriological methods. A monoclonal antibody (MAb) has been produced against Pasteuria biotype P-20spores, which binds to a putative glycan epitope shared by several polypeptides that are of different molecular masses and that occur in the spore envelope. The epitope detected by this MAb is found in endospores of *P. penetrans* isolates with a preference for *Meloidogyne arenaria* race 2, in *P. penetrans* with preferences for other Meloidogyne spp., and in Pasteuria isolates from other phytopathogenic nematodes. The epitope appears in infected female nematodes at a stage after, but not before, endospore formation can be observed. The disclosure introduces an antigen extraction procedure for soil-borne endospores and a rapid and sensitive ELISA to quantify Pasteuria spores in soil. Linear regression analysis of spore concentrations in soil samples versus absorbance produced good theoretical line fits for all ELISA formats evaluated. A tertiary detection system produced a minimum limit of less than 3000 spores/g of soil tested. Correlation of traditional and immunoassay spore quantitation data produced line fits of 0.99. Immunoblots comparing extracts from isolated spores and soil samples indicate the antigens extracted form the soil share molecular mass identity with those extracted from the isolated spores, providing confirmation that Pasteuria endospore-associated antigens are responsible for the ELISA signal. Cross-reactivity of the MAb extracts of other Gram positive bacteria committed to sporulation was not detected, indicating the epitope detected by the MAb is unique to the endospores of Pasteuria. The presence of the epitope on soil-borne spores and the ability to evaluate levels of *P. penetrans* as a measure of root-knot nematode infection should mitigate the need for the application of chemical nematicides where the levels of Pasteuria are adequate for the control of phytopathogenic nematode populations.

Further objectives and advantages of this invention will be apparent from the following detailed description of a presently preferred embodiment of a monoclonal antibody for detection of adhesins unique to the endospores of Pasteuria spp., the production of this antibody, and description of applications.

DESCRIPTION OF THE PREFERRED EMBODIMENT

Before explaining the disclosed embodiment of the present invention in detail it is to be understood that the invention is not limited in its application to the details of the particular arrangement shown since the invention is capable of other embodiments. Also, the terminology used herein is for the purpose of description and not of limitation.

A mature Pasteuria bacterium has endospores that are able to infect and suppress the soil levels of root-knot nematodes characterized by adhesins. A monoclonal antibody (MAb) has been produced against Pasteuria biotype P-20 spores, which has the property of binding a putative glycan epitope shared by a variety of molecular weight peptides present as a component of the Pasteuria spore envelope. Endospore and spore is used herein to describe the same entity.

The subject invention is a novel means for detecting the presence of and quantity of mature Pasteuria endospores useful in the biological control of nematodes. According to the subject invention, Pasteuria spores, such as those that infect the root-knot nematode Meloidogyne spp. or other specified host nematodes, are first prepared as monoclonal antibodies in mice that is directed against the P-20 isolate of *Pasteuria penetrans* by the method Mouse hybridoma cell line HL 1325 (2A4-1D10) was deposited with the American Type Culture Collection (10801 University Blvd., Manassas, Va. 20110-2209) on Nov. 15, 2001 as accession number PTA-3865.

In order to better understand the production of monoclonal antibodies (MAb) capable of detecting nematode adhesins associated with the presence of the Pasteuria genus, a detailed description of their production is set forth in the prior art referenced Charnecki Thesis (Chapter 2) which is incorporated herein by reference thereto.

The following Example describes a procedure to extract spore envelope antigen (UDC) from a soil matrix and application of an enzyme-linked immunosorbant assay (ELISA) to determine *Pasteuria penetrans* spore concentrations in field soil.

EXAMPLE (a) Materials and Methods
(i) Cultivation Methods.

*P. penetrans* isolate P-20 originated from *M. arenaria* (Neal) Chitwood race 1, from Levy County, Fla., was grown on tomato (*Lycopersicon esculentum* Mill. C. v. Rutgers) in green houses. P-20 spores were attached to the cuticles of 1 to 5 day-old Meloidogyne J2.via centrifugation at 4000 RPM for 5 min. Infected J2 were pipet transferred to steam pasteurized soil in pots containing Rutgers tomato. Inoculations of approx. 10,000 infected J2 per week were made for 3 weeks. 60 days following the last inoculation the roots were harvested and washed free of debris. The roots were placed in 1800 ml beaker containing 10% pectinase (Pomaliq), 50 mM NaAc, 0.1% $CaC2\mu$. The roots were digested for 2 days on an orbital shaker table (100 RPM) to free spore-filled female Meloidogyne from root galls. Females were collected by decanting onto a 600$\mu$m pore sieve nested on a 150 $\mu$m pore sieve under hard water spray. Spore-filled females, identified by a translucent cuticle, were hand-picked by pipet with the aid of a dissecting microscope. They were washed with dH20, ruptured and taken through woven polyester 21$\mu$m filter mesh (Spectra/Mesh) in a 13 mm Swinnex disc holder (Millipore). Recovered spores were washed in dH20 at 10,000×g for 5 min, repeated 2 times, and stored at 4° C. in 0.02% $NaN_3$ or frozen. Spores were enumerated on a hemocytometer (Fisher) under a 40×DIC objective.

(ii) Spore Antigen Extraction (UDC).

Spore preparations were added at a ratio of 1:3 (v/v) to a solution with a final concentration of 6.0 M urea, 0.005 M CHES pH 10, and 16 mM dithiothreitol (DTT) to generate pure culture UDC extracts with a spore equivalency of roughly $5e^{+05}$ spores/$\mu$l. Soil extractions are performed similarly. Soil to be extracted was air-dried, weighed (1.0 g [dry weight]), into 1.5 ml microfuge tubes. 100 $\mu$of $dH_2O$ (including spores when preparing standards) was added and vortexed. To this was added 300 μl of 1.33× stock UDC (DTT added just prior to extraction) followed by vortexing. Tubes were incubated for 2 hours at 37° C. or 30 min at 50° C. in a hot water bath with intermittent vortexing and sonic water bath exposure. Tubes were then centrifuged 10,000×g for 1 min and the supernate (UDC extract) removed by pipet. For soils, the supernate was again centrifuged at 10,000×g for 5 min to remove fines and the supernate transferred to a clean microfuge tube and stored at 4° C. or −20° C. Protein concentrations were determined by Coomassie blue binding assay (Bio-Rad Laboratories) utilizing the method of Bradford.

(iii) Soils.

Three soils (POL, POD, SHR) were utilized in preparing standards for soil spore extraction. POL is a highly leached quartz fine sand obtained from a Florida flatwoods site. POD was obtained from the same location but was located in a storm water depression and contained visibly more organic matter than POL. SHR is a calcareous loam from a pasture location. Soils evaluated for Pasteuria spores were collected at IFAS agricultural experimental stations and crop test plots in and around N. Central Florida and were obtained from the University of Florida Department of Entomology and Nematology, Gainesville, Fla.

(iv) Antibody Production.

The cultures producing P20 MAb were prepared by the Hybridoma Core Facility, University of Florida (ICBR), Gainesville, Fla. by immunization of BALB/c mice with $1\times10^6$ P20 spores. Selection of mass culture 2A41D10 was based upon distinct recognition of spore associated antigens from several different P. penetrans isolates. Purification of mouse ascites 2A41D10 HL 1325 98-3197.5 was achieved by gel filtration on a 1 m Sephacryl S-300 (Pharmacia) column eluted with 0.5 M NaCl and 0.02 M NaPO4 pH 7.0 run at room temperature at a flow rate of 0.6 ml/min, and collected in 6 ml fractions with a Gilson microfractionator. S-300 fractions exhibiting anti-spore activity were concentrated using Centriprep-10 microconcentrators (Amicon) and stored in 0.02% $NaN_3$ at 4° C.

(v) Identification of Spore-Forming Bacteria.

Spore forming organisms were isolated and cultured from test soils by heating the soil in sterile dH20 at 80° C. for 10 min and spreading on TSA plates. Single colonies where selected and repeatedly transferred to establish pure cultures. Cultures where sporulated in 125 ml flasks containing nutrient broth (Difco) on an orbital shaker at 100 RPM. Gram reactions where recorded on vegetative cells and sporulation was confirmed by endospore staining using malachite green, counter stained with safranin and visualized by phase contract microscopy. Isolates were identified by fatty acid methyl ester analysis (FAME) using a Hewlett-Packard gas chromatograph and the resulting profiles where statistically compared with profiles included in the Microbial Identification System (MIS) (Hewlett Packard) and MIDI Library, TSBA version 3.80.

(vi) SDS-PAGE Analysis.

UDC extracts were analyzed by sodium dodecyl sulfate-polyacrylamide gel electrophoresis (SDS-PAGE). A 6% stacking gel and a 12% (wt/vol) separation slab gel was prepared. Gels were transferred to nitrocellulose membranes in blotting buffer (192 mM glycine, 25 mM Tris-Base, 20% methanol), using a Mini Trans Blot Cell (BioRad) at 50 V constant voltage for 1.5 hrs. Membranes were blocked with 5% non-fat dried skim milk (Carnation) and 0.2% Tween 20 (v/v) in PBS (10 mM phosphate buffer, pH 7.6, 150 mM NaCl) overnight at 4° C. prior to immunoblotting. Prestained SDS-PAGE molecular weight markers (BioRad) were run on all gels.

(vii) Fluorescent Labeling of Spores.

$5\times10^7$ spores were centrifuged 10,000×g for 5 min and reconstituted in 500 μl of a 100 mM bicarbonate: carbonate solution of pH 9.1 containing 2.0 mg/ml flouroscein isothiocynate. Spores were incubated 2 hours at room temperature in the dark, centrifuged 10,000×g for 5 min and then reconstituted in dH20. The process was repeated until the supernate became clear.

(viii) Immunofluorescent Microscopy.

Circular cover slips (12 mm, #1 thickness), were washed in 70% ethanol and rinsed with excess dH20. Cover slips were added to a dish containing 1% Alician blue (cationic dye) in water, and heated to almost boiling for 10 min. The dye was poured off and the cover slips were thoroughly rinsed in dH20 and dried (light blue in color). Spores suspensions were applied to the cover slips and incubated 1 hr at 30° C. to adhere and dry. Slides were washed 3×in 400 ul PBS pH 7.3 containing 3% Bovine serum albumin (BSA). The slides were treated sequentially for 1 hr with primary antibody diluted in PBS (3% BSA) for 1 hr, rinsed 3 times as above, secondary Ab decorated with a fluorescent conjugate (FITC or TRITC) applied, washed 6 times and slips mounted on ethanol washed standard microscope slides using Fluoromount -G™ (Southern Biotechnology Associates, Inc.). Preparations were stored in the dark and visualized with a Nikon epifluorescent microscope fitted with a Episcopic Fluorescence attachment that housed a 495 nm excitation filter under 40×fluorescent, or 100×DIC objectives with oil.

(ix) Enzyme-Linked Immunosorbant Assay (ELISA).

UDC extracts were diluted to a range of between 50–0.005 ng/μl protein and used in an indirect standard assay and tertiary (amplification) ELISA. To 1 μl UDC extract was added 99 μl of coating buffer; CB (1.59 g Na2CO3, 2.81 g NaHCO3, 0.2 g NaN3 to 1000 ml dH20), and added to a Immulon-2 microtiter plates (Dynatech). Antigen was incubated 2 hr at room temperature or over night at 4° C., blocked with PBS containing 3% bovine serum albumin (PBS-BSA) for 30 min, washed 3× with 125 ul of PBS (0.01% Tween 20) pH 7.3 after incubation with each reagent. In the indirect ELISA plates were treated sequentially for 1 hr with purified -P20 MAb or mass culture -P20 supernatant, and anti-mouse IgM (u-chain specific) alkaline phosphatase conjugated. Bound conjugate was observed by addition of APS buffer containing 0.5 mM MgCl2 and 1.0 mg/ml p-nitrophenyl phosphate on a Biorad micro-plate reader at 405 nm. In the amplification ELISA, the plates were treated sequentially for 1 hr with -P20 MAb (1:1000 PBST 0.1%), biotinylated anti-mouse IgM u-chain specific Ab (1:500), NeutrAvidin™—HRP conjugated (Pierce). Bound conjugate was observed by addition of enzyme substrate 3,3',5,5'tetramethylbenzidine, Turbo TMB-ELISA™ (Pierce) and reactions were stopped with 100 ul 1.5 M $H_2SO_4$ and read at 450 nm.

(x)

RESULTS (a) Extraction of Antigens from Soil.

ELISA factoral evaluation of UDC extraction reagent components and extraction temperature regimes indicated that elevating temperature to 37° C. or above (50° C.) was needed to effectively extract spore envelope associated antigens. Varying extraction temperature and time between 37 and 50° C. and 0.5 to 2 hr, respectively, resulted in no change in extraction efficiency, thus providing a flexible window within this range in which to liberate antigen. The results indicate urea as the principle extraction component, followed by pH elevation with CHES buffer pH 10. Interestingly, dithiothreitol (DTT) had a minimum impact on releasing spore antigen efficiency.

(b) ELISA Sensitivity and Specificity.

Initial tests utilizing the standard indirect ELISA resulted in a minimum detection limit of ≧30,000 spores/g (0.056 ng/ul protein).

The tertiary ELISA provided the best quantitative data and the lowest detection limit. Incubation with -P20 MAb, followed by incubation with biotinylated anti-mouse IgM (u-chain specific) and detected with NeutrAvidin™—HRP reduced the detection limit over the standard assay 10 fold to ≈3,000 spores/g with respectable and reproducible line fits. Practically, the minimum detection limit for the ELISA was determined by the lowest concentration within the linear portion of the line fit. Theoretically the detection limit could be interpreted to approach 30 spores/g, however small absorbance values relative to sample standard deviations may limit accurate determination of spore concentration at concentrations less than 300 spores/g.

Concerns regarding the potential impacts of the varying physio-chemical properties of soils on spore antigen extraction efficiency and/or signal noise prompted experimentation with more than one type of test soil. Three soils where selected for spiking, extraction and ELISA for standard curve analysis. They represented typical agricultural soils, named POL, POD, and SHR. No significant variation in A 450 nm signal was evidenced for standards prepared in all three soils when evaluated collectively by Box plot analysis indicating that the soil properties had no impact on the soil extraction efficiency.

The MAb was challenged with UDC spore extracts of gram-positive spore forming organisms isolated from test soils and ATTC strains. The results of the ELISA -P20 MAb demonstrated no x-reactivity with the strains tested.

Antigen binding. Immunofluorescent microscopy images using fluorosceinisothiocyanate (FITC) conjugated anti-mouse IgM (u-chain specific) antibody show the MAb binds a super molecular architecture present as both loosely and tightly bound protein on the surface of the spore. UDC extracted P20 spore pellets are immuno reactive but less so than untreated spores. Mounted sporulated cultures of *B. subtillis* and *B. thuringiensis* spp. kurstaki where unreactive to the P20 MAb.

The -P20 MAb recognizes a glycopeptide involved in recognition and attachment to the nematode cuticle. Pre-incubation of spores or J2 with -P20 MAb prevents attachment at an $IC_{50}$ of $1.3e^{-10}$ M. FITC labeled spores (non-immunolabeled) show *Pasteuria penetrans* attachment to the juvenile *Meloidogyne arenaria* (nematode) host.

(c) SDS-PAGE and Western Blot Analysis.

UDC extracts of cropland test soil and spiked control soil were compared to P20 pure culture extracts using SDS-PAGE Western Blot analysis. The presence of P20 signature peptides in the soil UDC extracts were found.

Discussion of the Example Results

A monoclonal antibody 2A41D10 ( -P20 MAb) produced against *P. penetrans* (P20) spores has been shown to bind a putative glycan epitope shared by a variety of peptides of different mass present as a component of the spore envelope. The specificity of the -P20 MAb was evaluated by exposure to a number of both ATCC and gram-positive soil isolates using SDS-PAGE Western blot, ELISA, and immunofluorescent microscopy and found to be specific for Pasteuria spore envelope protein. *Pasteuria penetrans* harbors a unique and specific biochemical moiety present as component of its spore envelope that can be solubilized in a soil matrix and utilized for immunological detection, limited to the target organism.

Perhaps more important this example teaches an in-situ soil spore envelope extraction procedure (UDC) which can be employed to solubilize and liberate spore envelope protein from complex matrices for quantitative immunoassay detection either by ELISA or SDS-PAGE Western blotting. Soil extractions can be performed in less than one hour. Quantification of Pasteuria spores was demonstrated using three separate ELISA formats. The biotinylated MAb failed to improve the limit of detection but still resulted in a reliable and rapid assay. The teritary ELISA using a biotinylated anti-mouse antibody followed by NeutrAvidin™ (streptavidin derivative) produced the lowest detection limit of about 3,000 spores/g. The minimum detection limit of ≈3,000 spores/g falls within the level necessary to detect and evaluate soil nematode suppressivity.

The -P20 MAb demonstrated no cross-reactivity with any organisms with which it was challenged in this study. It appears that the epitope recognized by the -P20 MAb is unique to Pasteuria sp. Immunofluorecent micrographs showed significant antibody recognition of the spore exosporium and following UDC extraction this epitope was still visible as a halo surrounding the periphery of the spore cortex. It appears that this epitope is widely distributed in the inner and outer layers of the spore coat and is a predominant feature.

The foregoing example of the use of a monoclonal antibody (MAb) directed against a determinant (epitope) associated with the endospores of a strain of *Pasteuria penetrans* that parasitizes *Meloidopyne arenaria*, a destructive nematode pathogen of many agronomic, horticultural, and ornamental crops, illustrates its extraordinary potential as a probe for detection of mature spores. Since the antibody recognizes the epitope formed during spore maturation in the infected nematode host, it is a surprisingly useful probe for detecting the formation of mature and virulent spores. Further, since the epitope is found in endospores from several species of Pasteuria, but is absent from endospores of other soil-borne endospore-forming bacteria, its recognition manifests a surprising useful probe for the detection of levels of Pasteuria endospores in field and green house environments.

Based upon the results of the Example, the antibody constitutes a probe with which to 1) develop a convenient and accurate assay with which to estimate the levels of Pasteuria endospores in the soil, and thereby limit or preclude the application of chemical nematicides; 2) develop conditions for the cultivation and mass production of virulent endospores of Pasteuria spp. for direct application and biocontrol of phytopathogenic nematodes; and 3) define the chemical determinants involved in endospore attachment to a nematode host for the development of encumbering or targeting chemical entities specific for phytopathogenic nematodes.

This monoclonal antibody may be used: to detect the presence of endospores of *Pasteuria penetrans* during growth and maturation, and thereby prove the formation of mature endospores during cultivation outside of the nematode host. This antibody may thus be used for the development of mass cultivation protocols. This will permit the production of Pasteuria spores in quantities for their application as biocontrol agents for the suppression of root-knot and/or other phytopathogenic nematodes.

This monoclonal antibody may be used to monitor the levels of Pasteuria spores in the soil, and thereby be used to determine the extent to which further treatment is needed to suppress the infection of crop plants with root-knot nematodes or other important plant-parasitic nematodes.

This monoclonal antibody may be used to determine the complement of spore polypeptides bearing the adhesion epitope and thereby used to identify spore population with a preference for a particular species of nematode that parasitizes a particular crop plant.

It is envisioned that the process of the invention will make possible for the first time: the production of large quantities of mature viable endospores for field application for the biocontrol of phytopathogenic nematodes; and, field assays for the determination of levels of Pasteuria spp. endospores in soil and the extent to which a soil is suppressive for a particular phytopathogenic nematode.

The ability to reliably determine the quantities of mature endospores of *Pasteuria penetrans* and other species of Pasteuria will make it possible to develop protocols for their mass production. Such mass production will allow their field application for the control of root-knot and other susceptible phytopathogenic nematodes. There have been critical events that have occurred during the past 20 years that have drastically altered our ability to effectively manage all types of plant-parasitic nematodes, including root-knot nematodes. The highly effective and relatively economical nematicides, dibromochloropropane and ethylene dibromide, were suspended a number of years ago. Although the soil fumigant 1,3-dichloropropene remains available for use on most crops, it has imposing label restrictions, and to be effective, it must be applied at a high dosage (9 to 15 gallons/acre). This high dosage and the chemical's relatively high cost per gallon (ca.$10) remains an impediment to its successful use on most low value crops. This is especially true for agronomic and most horticultural crops. Currently, because of the Food Quality Protection Act, all the organophosphate and carbamate nematicides are under attack and suspension of several of these compounds is projected in the near future. For high value crops, the availability of the multi-purpose soil fumigant, methyl bromide, has already been limited to 25% of 1991 production levels, and its availability will be further restricted to 50% by 2001, 70% by 2003, and phased out completely by 2005. This phase out will have major repercussions for high value crops grown in the United States because other highly efficacious multi-purpose products, such as 1,3-dichloropropene-mencs (Vorlex®), currently are not being defended by their manufacturer. Other identified alternatives, such as 1,3-dichloropicrin, metam sodium, and methyl iodide, require special handling procedures, and must be applied with great care to assure they provide the efficacy needed.

Other important management strategies for plant-parasitic nematodes are limited in their usefulness. For example, many growers are unwilling to use crop rotation because they have established permanent irrigation systems in fields or because of the lack of suitable land availability. Although plant resistance in a few crops is an important tactic for nematode management, sources of resistant germplasm are limited or not available in most of the agronomic, vegetable, fruit, and ornamental crops that are grown in the United States. The use of compost and organic materials of various types as an aid for nematode management will be restricted because of fear of contamination from *E. coli* strains that cause human illness. Major food suppliers in Florida have already stated they will not accept produce treated with compost materials regardless of source (communicated by the Florida Fruit and Vegetable Assoc.). One can readily see that nematode management is very difficult at present and is likely to become more difficult in the future. Many times growers have no choice but to take their losses from nematodes as part of the business of growing crops in the nematode infested soils. It is particularly important for our fragile environment that benign alternatives to nematicides, such as that offered by biological control organisms be made available. The development of Pasteuria for the biocontrol of plant-parasitic nematodes may save several billions of dollars in crop losses.

The market for this technology are producers of agricultural crops, including agronomic crops, e.g., peanut, tobacco, cotton, soybean; vegetable crops, e.g., pepper, okra, carrot, tomato; fruit and nut crops; ornamental, e.g., turfgrass, landscape, flowering, and foliage plant, etc. This market is most prevalent in the southeastern and western United States where the commercial production of these crops is most susceptible to damage by root-knot nematodes as well as other important plant-parasitic nematodes. It is not limited to any particular region of the USA.

The market is particularly in need of this technology to develop effective alternatives to the use of chemical nematicides, which are facing suspensions because of their potential damage to humans, animals, and the environment. The technology, which will allow the development of Pasteuria, will allow a benign alternative to the use of chemical nematicides.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A method for identifying the presence of a Pasteuria spore in a soil sample, the method comprising the steps of:
   (a) providing the soil sample; and
   (b) analyzing the soil sample for the presence of an antigen comprising an epitope recognized by monoclonal antibody 2A41D10 (ATCC accession number PTA-3865);
      wherein presence of the antigen in the sample indicates that the soil sample contains the Pasteuria spore.

2. The method of claim 1, wherein the step (b) of analyzing the soil sample for the presence of the antigen comprises contacting the soil sample or an isolated portion of the soil sample with a probe that specifically binds the epitope recognized by monoclonal antibody 2A41D10.

3. The method of claim 2, wherein the probe is an antibody.

4. The method of claim 3, wherein the antibody specifically binds a glycan epitope.

5. The method of claim 3, wherein the antibody is a monoclonal antibody.

6. The method of claim 5, wherein the monoclonal antibody is 2A41D10.

7. The method of claim 2, wherein the probe is labeled with a detectable label.

8. A method for identifying the presence of a Pasteuria spore in a soil sample, the method comprising the steps of:
   (a) providing the soil sample;
   (b) extracting the soil sample with an extraction buffer to yield a soil extract; and
   (c) analyzing the soil extract for the presence of an antigen comprising an epitope recognized by monoclonal antibody 2A41D10;
      wherein presence of the antigen in.the soil extract indicates that the soil sample contains the Pasteuria spore.

9. The method of claim 8, wherein the step (c) of analyzing the soil extract comprises contacting the soil extract or an isolated portion of the soil extract with a probe that specifically binds the epitope recognized by monoclonal antibody 2A41D10.

10. The method of claim 9, wherein the probe is an antibody.

11. The method of claim 10, wherein the antibody specifically binds a glycan epitope.

12. The method of claim 10, wherein the antibody is a monoclonal antibody.

13. The method of claim 12, wherein the monoclonal antibody is 2A41D10.

14. The method of claim 9, wherein the probe is labeled with a detectable label.

15. The method of claim 8, wherein the step (c) of analyzing the soil extract comprises immobilizing the soil extract or the isolated portion of the soil extract on a substrate and then contacting the immobilized soil extract or the isolated portion of the soil extract with a probe that specifically binds the epitope recognized by monoclonal antibody 2A41D10.

16. The method of claim 15, wherein the probe is an antibody.

17. The method of claim 16, wherein the antibody specifically binds a glycan epitope.

18. The method of claim 16, wherein the antibody is a monoclonal antibody.

19. The method of claim 18, wherein the monoclonal antibody is 2A41D10.

20. The method of claim 15, wherein the probe is labeled with a detectable label.

21. A method for quantifying the approximate number of Pasteuria spores in a soil sample, the method comprising the steps of:

(a) providing the soil sample;

(b) extracting the soil sample with an extraction buffer to yield a soil extract; and (c) quantifying the amount of a Pasteuria spore marker in the soil extract or a portion of the soil extract, the marker being an antigen comprising an epitope recognized by monoclonal antibody 2A41D10;

wherein the amount of the Pasteuria spore marker in the soil extract correlates with the amount of Pasteuria spores in the soil sample.

22. The method of claim 21, wherein the step (c) of quantifying the amount of a Pasteuria spore marker in the soil extract or a portion of the soil extract comprises contacting the soil extract or a portion of the soil extract with a probe that specifically binds the epitope recognized by monoclonal antibody 2A41D10.

23. The method of claim 22, wherein the probe is an antibody.

24. The method of claim 23, wherein the antibody specifically binds a glycan epitope.

25. The method of claim 24, wherein the antibody is a monoclonal antibody.

26. The method of claim 25, wherein the monoclonal antibody is 2A41D10.

27. The method of claim 22, wherein the probe is labeled with a detectable label.

* * * * *